(12) United States Patent
Bebien et al.

(10) Patent No.: US 12,569,175 B2
(45) Date of Patent: Mar. 10, 2026

(54) BLOOD COMPONENTS COLLECTION AND SEPARATION MEDIA, BLOOD COMPONENTS COLLECTION AND SEPARATION DEVICE COMPRISING SAID MEDIA, AND BLOOD COMPONENTS SEPARATION AND EXTRACTION PROCESS IMPLEMENTING SAID MEDIA

(71) Applicant: Ahlstrom Oyj, Helsinki (FI)

(72) Inventors: Frédéric Bebien, Jardin (FR);
Stéphanie Pigeot Remy, Sainte Colombe (FR)

(73) Assignee: AHLSTROM OYJ, Helsinki (FI)

( * ) Notice: Subject to any disclaimer, the term of this patent is extended or adjusted under 35 U.S.C. 154(b) by 906 days.

(21) Appl. No.: 17/765,266

(22) PCT Filed: Oct. 2, 2019

(86) PCT No.: PCT/FI2019/050708
§ 371 (c)(1),
(2) Date: Mar. 30, 2022

(87) PCT Pub. No.: WO2021/064276
PCT Pub. Date: Apr. 8, 2021

(65) Prior Publication Data
US 2022/0338770 A1     Oct. 27, 2022

(51) Int. Cl.
*A61B 5/15*     (2006.01)
*B01D 39/16*     (2006.01)
(Continued)

(52) U.S. Cl.
CPC ...... *A61B 5/150755* (2013.01); *B01D 39/163* (2013.01); *B01D 39/2024* (2013.01);
(Continued)

(58) Field of Classification Search
None
See application file for complete search history.

(56) References Cited

U.S. PATENT DOCUMENTS 4,477,575 A     10/1984   Vogel et al.
4,816,224 A      3/1989   Vogel et al.
(Continued)

FOREIGN PATENT DOCUMENTS

CN     103285949 A     9/2013
CN     106770520 A     5/2017
(Continued)

OTHER PUBLICATIONS

International Search Report for International Application No. PCT/FI2019/050708; International Filing Date Oct. 2, 2019; Date of Mailing Jun. 4, 2020; 4 pages.
(Continued)

*Primary Examiner* — Lore R Jarrett
(74) *Attorney, Agent, or Firm* — CANTOR COLBURN LLP

(57)     ABSTRACT

The present invention relates to a blood components collection and separation media (1) comprising a substrate (3) having a maximal flow pore size enabling the retention of at least red cells on the surface of the substrate (3), the blood components collection and separation media (1) comprises boundary walls (7) forming a pattern (9) and being made of a hydrophobic resin, and the pattern (9) presenting: a collection zone (91); at least one storage zone (93) aimed at collecting at least one component of the whole blood sample (5); and at least one channel (95) connecting the collection zone (91) to the at least one storage zone (93), the channel (95) forming a bottleneck between the collection zone (91) and the storage zone (93). The present invention further relates to a blood components collection and separation
(Continued)

device and a blood components separation and extraction process.

20 Claims, 6 Drawing Sheets

(51) Int. Cl.
B01D 39/20 (2006.01)
G01N 33/49 (2006.01)

(52) U.S. Cl.
CPC ... G01N 33/491 (2013.01); B01D 2239/0421 (2013.01); B01D 2239/086 (2013.01); B01D 2239/1208 (2013.01); B01D 2239/1216 (2013.01)

(56) References Cited

U.S. PATENT DOCUMENTS

| | | | |
|---|---|---|---|
| 5,186,843 A | 2/1993 | Baumgardner et al. | |
| 5,454,946 A | 10/1995 | Heagle et al. | |
| 6,036,659 A * | 3/2000 | Ray | G01N 33/491 |
| | | | 600/573 |
| 9,539,572 B2 | 1/2017 | Blankenstein et al. | |
| 10,386,356 B2 | 8/2019 | Kelso et al. | |
| 2002/0053548 A1 | 5/2002 | Lee et al. | |
| 2006/0204403 A1 | 9/2006 | Federas | |
| 2007/0102362 A1 * | 5/2007 | Iida | B01L 3/502753 |
| | | | 210/656 |
| 2007/0178521 A1 | 8/2007 | Sakaino et al. | |
| 2010/0092979 A1 * | 4/2010 | Kelso | C12N 15/1017 |
| | | | 435/6.12 |
| 2014/0017124 A1 | 1/2014 | Lee et al. | |
| 2015/0014185 A1 | 1/2015 | Neijzen et al. | |
| 2015/0060353 A1 | 3/2015 | Neijzen et al. | |
| 2016/0109467 A1 | 4/2016 | Kolb et al. | |
| 2018/0207564 A1 | 7/2018 | Hennessey | |
| 2021/0068730 A1 * | 3/2021 | Johnson | A61B 5/155 |
| 2021/0378567 A1 | 12/2021 | Weidemaier et al. | |
| 2022/0268675 A1 | 8/2022 | Henion et al. | |
| 2022/0273209 A1 * | 9/2022 | Anderson | A61B 5/150022 |

FOREIGN PATENT DOCUMENTS

| | | |
|---|---|---|
| CN | 108646012 A | 10/2018 |
| WO | 2015014974 A1 | 2/2015 |
| WO | 2017017314 A1 | 2/2017 |

OTHER PUBLICATIONS

Written Opinion for International Application No. PCT/FI2019/050708; International Filing Date Oct. 2, 2019; Date of Mailing Jun. 4, 2020; 5 pages.

Chinese Office Action for the corresponding Chinese Application No. 201980102257.9, Date of Mailing: Oct. 8, 2024; 11 pages (no English translation).

* cited by examiner

BLOOD COMPONENTS COLLECTION AND SEPARATION MEDIA, BLOOD COMPONENTS COLLECTION AND SEPARATION DEVICE COMPRISING SAID MEDIA, AND BLOOD COMPONENTS SEPARATION AND EXTRACTION PROCESS IMPLEMENTING SAID MEDIA

CROSS REFERENCE TO RELATED APPLICATIONS

This application is a National Stage application of PCT/FI2019/050708, filed Oct. 2, 2019, which is incorporated by reference in its entirety herein.

FIELD OF THE INVENTION

The present invention relates to collection and separation of biological fluids. More particularly, the present invention relates to a blood components collection and separation media, a use of this media in a blood separation and extraction process and a blood components collection and separation device implementing such a blood components collection and separation media. More particularly, the present invention relates to devices used as blood components collector and separator.

BACKGROUND ART

Biological samples are frequently used in laboratory and clinical settings to analyze various components in the samples, such as blood samples for example. The biological sample is frequently processed in a liquid form. Accordingly, the liquid sample is collected, handled in a collection facility, transported to a laboratory and stored. Activities surrounding a liquid sample (such as blood for example) present various problems including the risk of container breakage or leakage which causes loss of sample and potential contamination and/or infection risk, sample instability during shipment and storage, transport carrier restrictions related to transport of liquid biohazard materials.

In order to avoid such problems, various dried sample devices and methods have emerged. The blood as dried sample is not considered as biohazard material and may be transported through a classical delivery service just as any other package. For this purpose, the blood sample (a few drops generally) is disposed onto a paper and is allowed to dry. Moreover, in order to improve the efficiency of those devices and methods, some papers are configured for separating the blood components.

Indeed, blood is made up of two fractions: blood cells and the liquid in which the blood cells are suspended. The liquid is known as blood plasma ("plasma") and is a proteinaceous fluid which may include other smaller cells and dissolved proteins, such as serum albumins, globulins, and fibrogens, glucose, clotting factors, electrolytes (Na', Cat', $Mg^{2+}$, $HCO_3^-$, $Cl^-$, etc), hormones and carbon dioxide. The main eukaryotic cell type present in blood are the red blood cells (erythrocytes), white blood cells (leucocytes) and platelets, although other cell types may be detected as well. Erythrocytes constitute about a half of volume of blood sample.

The separation of red blood cells from the plasma in a blood sample is of great importance for the purpose of rapid diagnosis of plasma constituents in clinics, hospitals, and in field conditions, because red blood cells can weaken the sensitivity of the assay. Also the whole blood can cause undesired chemical interference. For example, hemoglobin that is release from red blood cells can affect the performance of certain clinical assays due to the iron heme group, which can act as a catalyst.

During the separation of erythrocytes from the fluid fraction, it is further important that the red blood cells not lyse or rupture, which may cause the release of internal constituents into the plasma and also pollute the plasma sample. In order to obtain plasma from a whole blood for testing, basically four different kinds of techniques are used: viz. gravity, pressure drop, capillary flow, and centrifugal force based techniques.

Assays which are to be performed in field conditions should be inexpensive, and the samples should be disposable. These aims cannot be properly met with some of the techniques mentioned above. Pressure drop and centrifugal force require specialized equipment, implementing pumps and centrifuges making them unsuitable for field use. Then, gravity based techniques are too slow for field use.

Therefore, assays for separating whole blood into red blood cells and plasma have been developed which are based on capillary flow in lateral flow assay devices. A number of such assays are disclosed in the art.

U.S. Pat. Nos. 4,477,575 and 4,816,224 describe medias using layers of glass microfibers to separate erythrocytes from whole blood. Papers containing 100% glass microfibers of the proposed kind are inherently weak and require extreme care in handling. Although strength can be enhanced through the use of binders, some binders can cause interferences with the assay or make the sheet hydrophobic.

Another approach comprises the use of a single-layered medium made of a composite of glass microfibers, cellulose fibers and synthetic staple fibers. In this respect, reference is made to U.S. Pat. No. 5,186,843.

Although the blood separation medias proposed in the past are suitable for their intended purpose, some improvements are still desired.

Generally, filtration on lateral flow assay devices is hampered by inadequate speed, as whole blood is rather viscous and begins clot in air. A standard blood filter must have pores smaller than the size of a red blood cell. This is due to the folding that the red blood cells are capable of. When these folded cells pass through the pores some of them become lodged in the pore, blocking it and decreasing the filtration efficiency. This also reduces the number of pores available for the passage of plasma and decreases the total amount of plasma that passes through the filter per unit time.

Further, damage or rupture of the cells may occur. This is especially true if the fiber that makes up the nonwoven is glass, such as the ones suggested above in the U.S. Pat. No. 5,186,843.

Glass fibers still give good separation of erythrocytes from blood due to the affinity of red blood cells to glass which provides for efficient slowing up of the erythrocytes in capillary flow. However, even if red blood cells present a good affinity for glass fibers, those glass fibers may increase hemolysis phenomenon and the separation of the several blood component could be not so efficient. To solve this prior art problem, it is known from the international patent application WO 2017/017314, filed by the Applicant, a blood collection and separation media preventing this hemolysis phenomenon. The hemolysis phenomenon is prevented by using a resin aimed at coating at least partially the glass fibers, also preventing this hemolysis phenomenon. However, even if this blood collection and separation media offers good separation results of the several blood components, the deposition of the whole blood sample has to be done with precision and the zone to be for example punched or eluted to recover the desired constituent of the whole blood sample can be difficult to identify. Moreover, this blood collection and separation media can be difficult to use in an automated process for collecting and separating blood components from a whole blood sample.

SUMMARY OF THE INVENTION

The present invention is aimed at solving at least partially the drawbacks of the prior art discussed here-above by providing a blood components collection and separation media facilitating the deposition of the whole blood sample.

Another aspect of the present invention is to provide a blood components collection and separation media having easily identifiable zones for the several constituents of the whole blood sample after their separation on the blood components collection and separation media and preventing hemolysis phenomenon during the separation of the several constituents of the whole blood sample.

A further aspect of the present invention, different from those recited before, is to provide a blood components collection and separation device that may be used in an automated process.

In order to meet, at least partially, at least one of the here-above recited objective, the present invention is directed to a blood components collection and separation media comprising a substrate aimed at being wetted by a whole blood sample, the substrate having a maximal flow pore size comprised between 8 μm and 35 μm, such maximal flow pore size enabling the retention of at least red cells in the substrate, the blood components collection and separation media further comprising boundary walls which form a pattern into said substrate, said boundary walls being made of a hydrophobic resin, and the pattern presents:

- a collection zone aimed at receiving the whole blood sample;
- at least one storage zone aimed at storing at least one component of the whole blood sample after its separation through the substrate; and
- at least one channel connecting the collection zone to the at least one storage zone, said channel forming a bottleneck between the collection zone and the storage zone.

The presence of the channel forming a bottleneck between the collection zone and the storage zone enables the diffusion of the plasma to the at least one storage zone and the retention of the red blood cells in the collection zone. Thus, the identification of the zones containing a specific constituent of the whole blood sample can be easily identified.

Moreover, the deposition of the whole blood sample can be done anywhere within the collection zone without impacting the diffusion of the plasma in the storage zone, also simplifying the deposition process of the whole blood sample on the blood components collection and separation media.

The blood components collection and separation media according to the present invention can further present one or more of the following features, taken alone or in combination.

According to a particular embodiment, the maximal flow pore size of the substrate is preferably comprised between 9.5 μm and 10.5 μm.

The substrate may further have a minimal flow pore size comprised between 0.5 μm and 2 μm, and preferably comprised between 0.9 μm and 1.3 μm.

According to a specific embodiment, the substrate may have a mean flow pore size comprised between 2.5 μm and 5 μm.

According to this specific embodiment, the mean flow pore size is preferably comprised between 3 μm and 3.5 μm.

The hydrophobic resin forming the boundary walls may be chosen among photo-curable resins, more preferably UV-curable resins, or thermosetting resins.

More particularly, the hydrophobic resin may be chosen among fluorinated resins, modified fluorinated resins, latexes, glycol ether acrylates, acrylate esters, or a combination of thereof.

According to a specific embodiment, the hydrophobic resin is chosen among polymethyl methacrylate (PMMA) or polydimethylsiloxan (PDMS).

According to a particular embodiment, the collection zone of the pattern may have a substantially parallelogram shape.

According to this particular embodiment, the at least one storage zone may be disposed at an angle of the substantially parallelogram shape of the collection zone.

According to a variant of this particular embodiment, the pattern may present as many storage zones as the collection zone has angles.

Alternatively or in addition, the at least one storage zone may have a substantially circular shape.

According to a first embodiment, the storage zone is aimed at being punched.

According to a second embodiment, the at least one component stored in the storage zone is aimed at being eluted.

According to a third embodiment, the collection zone is aimed at being punched.

According to an aspect, the at least one channel has a length comprised between 1 mm and 5 mm and a width comprised between 1 mm and 3 mm.

According to a specific embodiment, the substrate may be a fibrous web comprising:

- first fibers, said first fibers being chosen among glass micro-fibers or synthetic micro-fibers;
- second fibers, said second fibers being chosen among fibrillated fibers; and
- a hydrophilic binder.

The hydrophilic binder may be chosen among latex binders.

According to an alternative, the hydrophilic binder may be chosen among polyvinyl alcohol binders.

According to a further alternative, the hydrophilic binder may be chosen among styrene-butadiene binders.

According to another alternative, the hydrophilic binder may be chosen among vinyl-acetate binders.

According to a variant, the hydrophilic binder may be chosen among polysaccharide binders.

According to another variant, the hydrophilic binder may be chosen among protein binders.

According to a particular embodiment, the first fibers may have a diameter of less than 5 μm, and preferably comprised between 0.4 μm and 1 μm.

Alternatively or in addition, the first fibers may have a specific surface area greater than 1.5 m²/g.

Moreover, the first fibers may have a length/diameter ratio greater than 100 and more preferably greater than 500.

The first and second fibers can be mixed together.

According to a particular embodiment, the second fibers are cellulosic-based fibers, and in particular cotton linters, lyocell, or viscose fibers.

According to the specific embodiment described here-above, the fibrous web may comprise between 5 and 7% by weight of the hydrophilic binder.

According to a particular embodiment, the fibrous web may comprise between 50 and 99% by weight of the first fibers, in particular between 70 and 98% by weight, and between 1 and 50% by weight of the second fibers, 100% by weight corresponding to the formed fibrous web.

The hydrophilic binder can cover at least partially the first fibers of the fibrous web.

According to an aspect, the fibrous web may comprise at least one additive for improving a characteristic of the substrate.

According to an embodiment of this aspect, the at least one additive can be a stabilizing agent of biomarkers extracted from the plasma, such as an animal protein as bovine serum albumin (BSA), gelatin derivatives, or sucrose.

According to a specific embodiment, some of the boundary walls or all of them extend through at least a part of, or through the whole depth of the substrate. In particular, the boundary walls preferably extend at least through the whole depth of the substrate.

According to a particular embodiment, the boundary walls forming the pattern can exceed one surface of the substrate.

The collection zone may be dimensioned to receive a volume of whole blood sample comprised between 50 and 500 µL.

As an alternative or in addition, the collection zone may further contain a salt capable of achieving at least partial crenation of red cells, the salt being chosen from the group of alkali metal and alkaline earth metal halogenides and sulfates, and hydrochlorides of organic bases.

According to this alternative, the salt may be chosen among calcium chloride, potassium sulfate, or guanine hydrochloride.

Other suitable salts are manganese chloride, potassium chloride, magnesium chloride, and sodium chloride.

The salt may be present at a concentration in the substrate comprised between 1 and 25% of the total weight of the substrate, and more particularly between 10 and 20% of the total weight of the substrate.

According to a particular embodiment, the pattern may present a collection zone having a square shape and four storage zones disposed at each angle of the collection zone, each storage zone having a circular shape and being connected to the collection zone by a channel forming a bottleneck between the collection zone and the storage zone associated.

The at least one storage zone may present pre-perforations facilitating its punching.

The present invention further relates to a blood components collection and separation device, aimed at collecting and separating at least one component of a whole blood sample, the blood components collection and separation device comprising at least the blood components collection and separation media as defined here-above and a frame surrounding the blood components collection and separation media.

The blood components collection and separation device according to the present invention may further comprise one or more of the following features.

According to a particular embodiment, the frame may be made of cardboard.

The frame can enable the blood components collection and separation device to be taken and processed by an automaton.

The blood components collection and separation device may be square shaped or rectangular shaped.

According to a first specific embodiment, the frame can present a triangle printed on one corner, said triangle being aimed at enabling an automaton to recognize the direction of the blood components collection and separation device.

According to a second specific embodiment, the frame can present a notched angle, said notched angle being aimed at enabling an automaton to recognize the direction of the blood components collection and separation device.

Moreover, the blood components collection and separation device may present a length and a width configured to be compatible with an automaton.

Optionally, the blood components collection and separation device may present at least two indicators of the collection zone, said indicators being configured for enabling an automaton to detect the collection zone.

According to a first variant, the indicators can be disposed on the blood components collection and separation media outside the pattern.

According to this first variant, the indicators can be printed by inkjet or made of the hydrophobic resin forming the pattern.

According to a second variant, the indicators can be disposed on the frame of the blood components collection and separation media.

Alternatively or in addition, the frame may present an identification zone configured to enable an identification of the blood components collection and separation device.

The identification zone can comprise a symbol that can be read by an automaton or by a human.

According to a specific embodiment, the frame can comprise at least two elevating elements, and preferably four elevating elements, said elevating elements being configured to be in contact with a support onto which the blood components collection and separation device is aimed at being disposed to elevate the blood components collection and separation media from said support and prevent any contact between the blood components collection and separation media and the support.

The present invention further relates to a blood components separation and extraction process, implementing a blood components collection and separation media as defined here-above and implementing the following steps:

deposition of a whole blood sample in the collection zone;
absorption of the whole blood sample onto the substrate;
retention of the red cells, the white cells and the platelets on the substrate in the collection zone;
diffusion of at least one component through the substrate to the at least one storage zone; and
extraction of at least one target component stored in the substrate of the blood components collection and separation media.

The blood components separation and extraction process may further comprise one or more of the following features.

According to a first embodiment, the at least one target component is stored in the at least one storage zone and the extraction step of said at least one target component is performed by punching at least one part of said at least one storage zone or by eluting said at least one target component from the at least one storage zone.

According to a second embodiment, the at least one target component is stored in the collection zone and the extraction step of said at least one target component is performed by punching at least one part of said collection zone or by eluting said at least one target component from the collection zone.

The whole blood sample deposited in the collection zone may have a volume comprised between 50 μL and 500 μL.

According to a particular embodiment, the target component aimed at being extracted from the whole blood sample can be plasma.

According to an alternative, the target component aimed at being extracted from the whole blood sample can be DNA, said DNA being stored in the white cells.

According to a further alternative, the target component aimed at being extracted from the whole blood sample can be lipids, said lipids being stored in the red cells.

According to a particular embodiment, the blood components separation and extraction process can be aimed at being implemented by an automaton.

BRIEF DESCRIPTION OF THE DRAWINGS

Further advantages and characteristics will be better identified and understood with the following description, given as an illustrative and not a limitative way, and the enclosed drawings in which.

DESCRIPTION OF EMBODIMENTS

Figure 1:
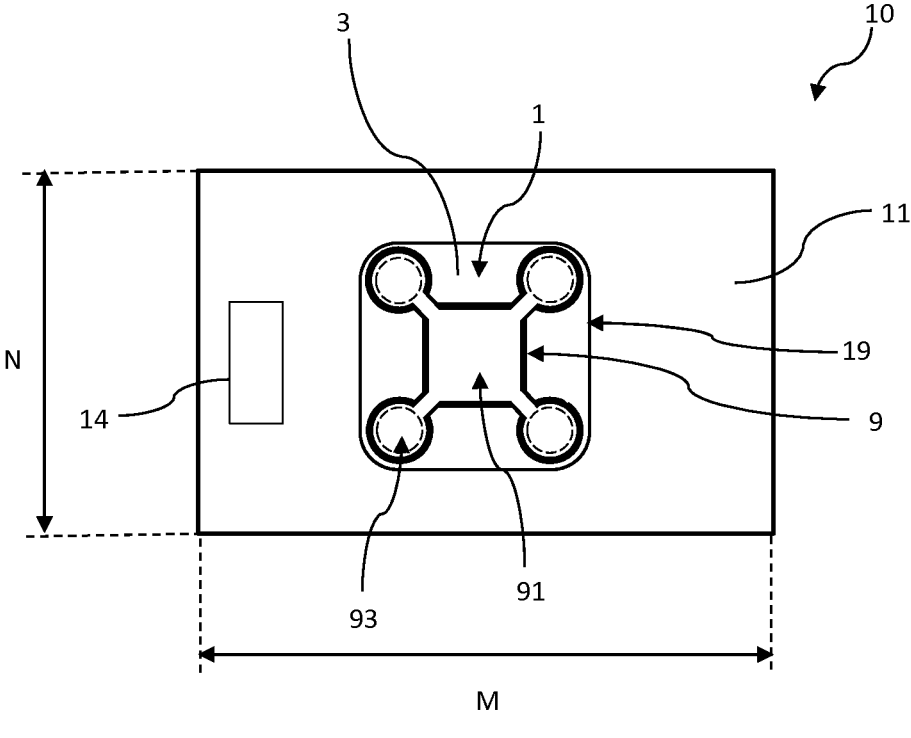
FIG. 1 is a schematic representation of a top view of a blood components collection and separation device according to the invention.

On these figures and in the following description, the same elements have the same numeral references.

Moreover, the embodiment(s) in the following description are only to be considered as examples. Although the description refers to one or several embodiments, this does not mean inevitably that every reference concerns the same embodiment, or that characteristics apply only to a single embodiment. Simple characteristics of various embodiments can be also combined to provide new embodiments that are not explicitly described.

In the following, it is referred to a first and second element and/or parameter. Such indexation is only intended to differentiate two elements and/or parameters that are close but not identical. Such indexation can be interchanged without impacting the disposition or the implementation of those elements and/or parameters. Furthermore, this indexation is not intended to appreciate in time or in space the disposition of those first and second elements and/or parameters.

In the following, the following definitions are used.

A "whole blood sample" is any sample of blood from human or animal origin, stabilized or not, constituted by 55% plasma and 45% figured elements comprising erythrocytes (red blood cells), leucocytes (white blood cells) and platelets.

"Plasma" in whole blood generally comprises water and proteins. Typically, plasma contains about 92% water, 7% albumin, gamma globulin, anti-hemophilic factor and other clotting factors along with about 1% mineral salts, fats, hormones and vitamins, the percentage being calculated from the total weight of blood.

A "target component" is a component of a whole blood sample 5 aimed at being titrated after its extraction, such component being stored in the red cells 51, the platelets 52, the white cells 53, or the plasma 55.

"Pore size" (in μm) can be determined by the American Society of Testing and Materials (ASTM) Standard 316-03 (2011).

The maximum pore size, minimum pore size and mean flow pore size can measured using a technique known as capillary flow porometry. A sample of the nonwoven fibrous web sample is first wetted with a wetting fluid such that all the pores in the sample are filled. A nonreacting gas of increasing pressure is applied to one side of the wet sample to displace the wetting fluid from the pores. The gas pressure and gas flow rate downstream of the sample are measured and plotted for the wet sample. After the sample is dry, the test is repeated to plot a similar curve for the dry sample.

The "maximum pore size" is calculated from the bubble point, i.e., the gas pressure at which air flow through the wet sample is first detected. The term "mean flow pore size" is calculated from the gas pressure at which the flow through a wetted sample is 50% of the flow through the dry sample. The term "minimum pore size" is calculated from the pressure at which the wet flow rate curve merges with dry flow rate curve. The term "pore size range" is defined as the difference between the "maximum pore size" and the "minimum pore size" (i.e. Pore Size Range=Maximum Pore Size−Minimum Pore Size).

According to FIG. 1, there is represented a blood components collection and separation device 10 aimed at collecting and separating at least one component of a whole blood sample 5 (represented on FIGS. 7A-8B). The blood components collection and separation device 10 comprises at least a blood components collection and separation media 1 and a frame 11 surrounding the blood components collection and separation media 1. The frame 11 has a window 19 showing the blood components collection and separation media 1.

The blood components collection and separation device 10 presents a length M and a width N. According to the particular embodiment of FIG. 1, the length M of the blood components collection and separation device 10 can be comprised between 75 and 100 mm and its width N can be comprised between 40 and 60 mm for example. According to an aspect, the length M and the width N of this blood components collection and separation device 10 can be configured to be compatible with an automaton and more particularly with the dimensions of a rack aimed at holding the blood components collection and separation device 10 and a gripper aimed at picking up the blood components collection and separation device 10 of such automaton in order to allow an automation of the blood depositing tasks for example. Accordingly, the length M and the width N of this blood components collection and separation device 10 can be adapted to the requirement for the automation. More particularly, the length M and the width N of the blood components collection and separation device 10 are determined by the frame 11. Accordingly, it is easy to adapt the blood components collection and separation device 10 to the requirements for the automaton without needing a modification of the dimensions of the blood components collection and separation media 1.

The frame 11 can be made of cardboard (also called "paperboard"). Advantageously, cardboard is a rigid material generally low cost and biodegradable. Such frame 11, made of cardboard, also enables a reduction of the production costs of this blood components collection and separation device 10 as well as reducing the amount of non-biodegradable waste. Furthermore, even if this blood components collection and collection device 10 is aimed at being used by a human or by an automaton, this device has to present a minimal rigidity in order at least to enable this device be easily taken and processed by the human or the automaton. The use of cardboard for the frame 11 enable to easily adapt the length M and the width N of the blood components collection and separation device 10 as such material is easy to cut for example. This frame 11 can be further constituted by other rigid materials such as wood, plastic, metal.

According to the particular embodiment of FIG. 1, the blood components collection and separation device 10 may be square shaped or rectangular shaped. Such shapes are easy to produce and can further be produced quickly and in a cost efficient manner by at least decreasing the wastes. Furthermore, such shapes can be easily taken by a human or an automaton and can also be recommended for an automation of the blood deposition and separation processes.

Optionally and as represented on FIG. 1, the frame 11 can present an identification zone 14 configured to enable an identification of the blood components collection and separation device 10 and/or of the sample deposited on the blood components collection and separation media 1. The identification zone 14 comprises a symbol that can be read by an automaton or by a human. Such symbol can for example be a QR code, a bar code, numbers, a name, or any other symbols enabling the identification of the sample deposited on the blood components separation and collection device 10. According to a variant, the identification zone 14 may comprise a RFID enabling the recognition of the blood components collection and separation device 10. Such identification zone 14 may enable to avoid mistakes between samples in the case were several samples are collected at a same point or different points from several patients for example.

Figures 2, 3B:
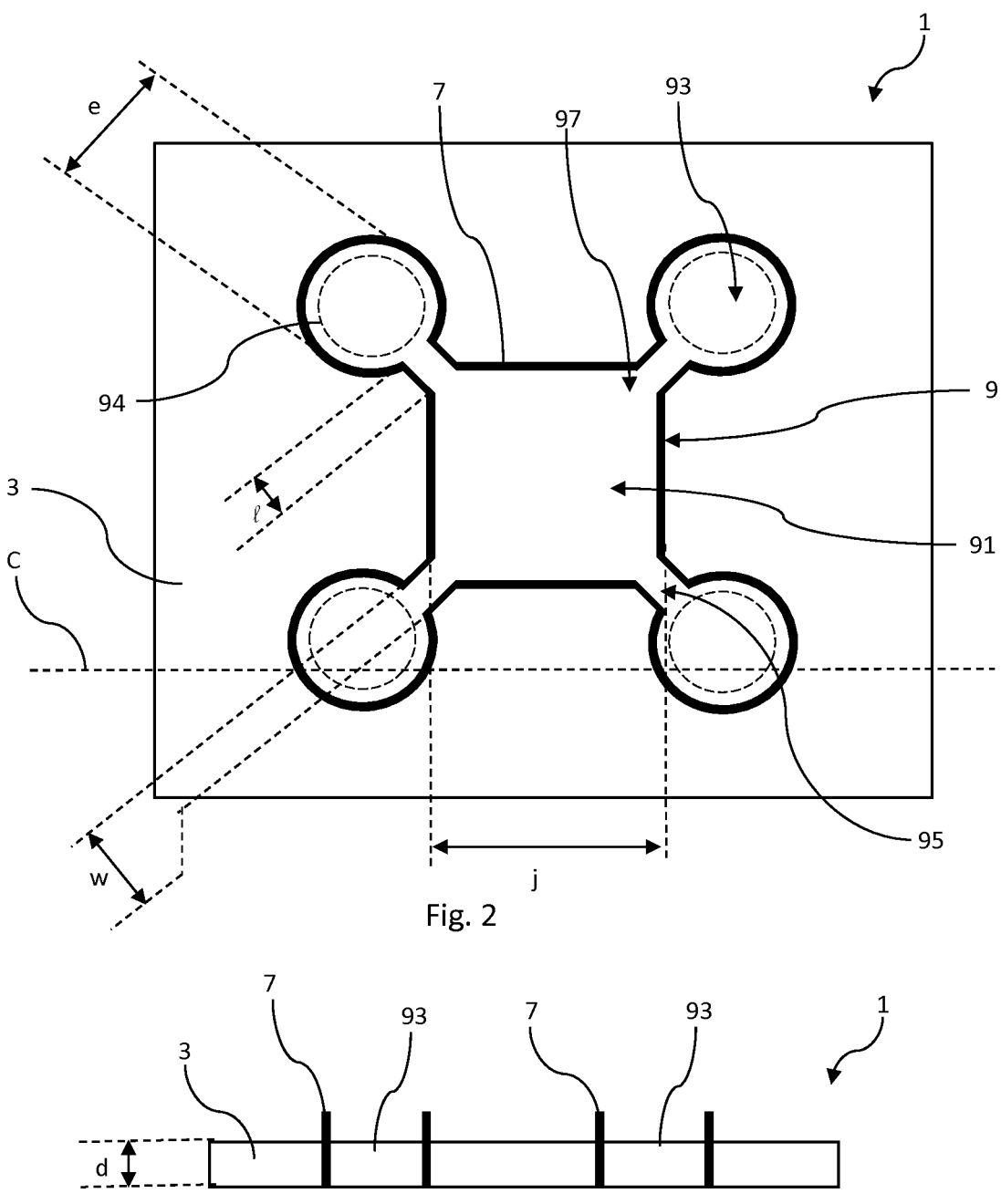
FIG. 2 is a schematic representation of a top view of a blood components collection and separation media implemented in the blood components collection and separation device of FIG. 1.
FIG. 3B is a schematic cut view of the blood components collection and separation media of FIG. 2 according to a second particular embodiment.

FIG. 2 represents the blood components collection and separation media 1 in more details. The blood components collection and separation media 1 comprises a substrate 3 and boundary walls 7.

In the embodiments depicted, the substrate 3 is aimed at, and preferably capable of being wetted (for example fully wetted), by the whole blood sample 5. The substrate 3 has a maximal flow pore size comprised between 8 μm and 35 μm, such maximal flow pore size enabling the retention of at least red cells 51 in the substrate 3. More particularly, the substrate 3 presents a maximal flow pore size configured for the retention of the red blood cells 51 and the white blood cells 53 at its surface. According to a particular embodiment, the maximal flow pore size of the substrate 3 can be preferably comprised between 9.5 μm and 10.5 μm. In addition or as a further variant, the substrate 3 further can have a minimal flow pore size comprised between 0.5 μm and 2 μm, and preferably comprised between 0.9 μm and 1.3 μm. Then, still in addition or as an alternative, the substrate 3 can have a mean flow pore size comprised between 2.5 μm and 5 μm, and preferably comprised between 3 μm and 3.5 μm. Such characteristics for the substrate 3, taken alone or in combination, enable the substrate 3 to separate plasma 55 (represented on FIG. 9) from the other components of the whole blood sample 5 (represented on FIG. 7A-8B) such as red cells 51 (represented on FIG. 9), platelets 52 (represented on FIG. 9), or white cells 53 (represented on FIG. 9 too). Indeed, the several components of the whole blood sample 5 have different sizes. For example the red blood cells 51 have a mean diameter of 7 μm, the platelets 52 have a mean diameter generally comprised between 1.5 and 3 μm, the white blood cells have a mean diameter of 12 μm, and the plasma 55 is mostly constituted by water. With such specific pore sizes, the red blood cells 51, the platelets 52 and the white blood cells 53 will be retained at the surface of the substrate 3 and/or into it for example.

According to the particular embodiment of FIG. 2, the substrate 3 can be a fibrous web comprising first fibers, second fibers and a hydrophilic binder. The first fibers are chosen among glass micro-fibers or synthetic micro-fibers and the second fibers are chosen among fibrillated fibers. Glass fibers are well known in the art to have a good affinity with red blood cells 53. Accordingly, red blood cells 53 will adhere on the glass fibers and a slow up of the movement of the red blood cells take place relative to the movement of the plasma 55 through the substrate 3 also enabling a separation of the constituents of the whole blood sample 5. However, some hemolysis phenomenon of those red blood cells 53 can be observed due to the cutting properties of such glass fibers. To prevent such hemolysis phenomenon of the red blood cells 53, the hydrophilic binder covers at least partially the first fibers of the fibrous web. It has been shown that between 5 and 7% by weight of the hydrophilic binder in the fibrous web enables prevention of the hemolysis phenomenon. Furthermore, the hydrophilic binder may be chosen among latex binders, polyvinyl alcohol binders, styrene-butadiene binders, vinyl-acetate binders, polysaccharide binders, or protein binders.

The first fibers may present one or more of the following characteristics: a diameter of less than 5 μm, and preferably comprised between 0.4 μm and 1 μm, a specific surface area greater than 1.5 m²/g, a length/diameter ratio greater than 100 and more preferably greater than 500. Such characteristics for the first fibers of the substrate 3 enable to retain the red blood cells 51 through the substrate 3 and also slow down their diffusion speed through the substrate 3 compared to the plasma 55 and enable the separation of the components forming the whole blood sample 5 through this substrate 3. Such characteristics for the first fibers will have improved affinity with red blood cells 51.

The second fibers can be cellulosic-based fibers, and in particular cotton linters, lyocell, or viscose fibers. According to the particular embodiment of FIG. 2, the first and second fibers, forming the substrate 3, can be mixed together. More particularly, the fibrous web can comprise between 50 and 99% by weight of the first fibers, in particular between 70 and 98% by weight, and between 1 and 50% by weight of the second fibers, 100% by weight corresponding to the formed fibrous web. Such repartition between the first and second fibers enable the substrate 3 to be well designed to separate the several constituents of the whole blood sample 5.

Optionally, the fibrous web can comprise at least one additive for improving characteristics of the substrate 3. For example, this additive can be a stabilizing agent for biomarkers extracted from the plasma 55, for example an animal protein as bovine serum albumin (BSA) or gelatin derivatives. According to another aspect, this stabilizing agent can be sucrose to retain humidity and also preserve the biomarkers.

Figure 3A:
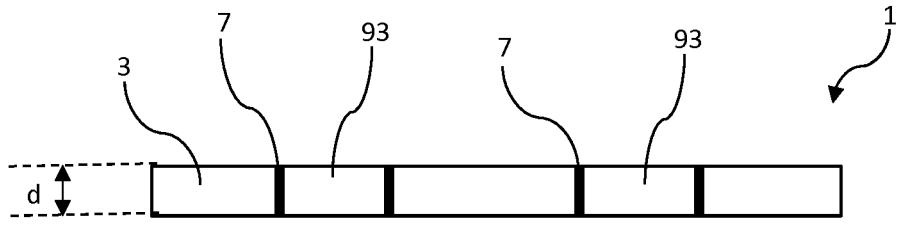
FIG. 3A is a schematic cut view of the blood components collection and separation media of FIG. 2 according to a first particular embodiment.

In the embodiment shown FIGS. 2 to 3B, the boundary walls 7 extend at least through the whole depth d of the substrate 3 and form a pattern 9 into said substrate 3. FIGS. 3A and 3B are cut views of the blood components collection and separation media 1 of FIG. 2, said views being cut according to the axis C represented on FIG. 2. According to the particular embodiments represented here, the depth d of the substrate 3 may be comprised between 50 and 1000 μm, and more preferably between 200 and 500 μm. According to the specific embodiment represented on FIG. 3A, the boundary walls 7 only extend through the whole depth d of the substrate 3. Moreover, and according the specific embodiment represented on FIG. 3B, the boundary walls 7 forming the pattern 9 can extend outside or above one surface of the substrate 3. More particularly, the boundary walls 7 can extend from the surface of the substrate 3 up to a distance equal to 80% of the depth d of the substrate 3. According to this second particular embodiment, it is possible to deposit on the substrate 3 a higher volume of whole blood sample 5 (represented in FIGS. 7A-8B) compared to the volume that can be disposed on the blood components collection and separation media 1 represented on FIG. 3A.

The boundary walls 7 are made of a hydrophobic resin. The use of a hydrophobic resin extending at least through the whole depth d of the substrate 3 enables to maintain the whole blood sample 5 into the pattern 9 and also the separation of its several components in this pattern 9. Furthermore, the use of a hydrophobic resin for forming the boundary walls 7 enables the plasma 55 to be easily guided without any risk for this constituent to diffuse outside the pattern 9. More particularly, the hydrophobic resin forming the boundary walls 7 can be chosen among photo-curable resins, more preferably UV-curable resins, or thermosetting resins. According to another embodiment, the hydrophobic resin can be chosen among fluorinated resins, modified fluorinated resins, latexes, glycol ether acrylates, acrylate esters, or a combination of thereof. More particularly, the hydrophobic resin can be chosen among a polymethyl methacrylate resin (PMMA) or a polydimethylsiloxan resin (PDMS). Such hydrophobic resins can be applied onto the substrate 3 without any contact with the fibrous web, such as by a non-contact dispensing system for example. According to another embodiment, the hydrophobic resin can be applied onto the substrate 3 with contact with the fibrous web, such as by screen printing for example.

Still referring to FIG. 2, the pattern 9 presents a collection zone 91, at least one storage zone 93 and at least one channel 95 connecting the collection zone 91 to the at least one storage zone 93, said channel 95 forming a bottleneck between the collection zone 91 and the storage zone 93. The collection zone 91 is aimed at receiving the whole blood sample 5. Furthermore, the at least one storage zone 93 is aimed at storing at least one component of the whole blood sample 5 after its separation through the substrate 3. The bottleneck form of the at least one channel 95 direct the separated plasma 55 from the whole blood sample 5 to the at least one storage zone 93, the separation of the plasma 55 from the whole blood sample 5 being performed by the substrate 3 as it will be explained in more details below. Moreover, this at least one channel 95 enables the repartition of the whole blood sample 5 in all the collection zone 91 whatever the deposition zone of the whole blood sample 5 in this collection zone 91. Accordingly, the pattern 9 formed by the boundary walls 7 enables to dispose the whole blood sample 5 at any place in the collection zone 91, the diffusion of the several constituents of the whole blood sample 5 being then controlled by the substrate 3, at least due to its porosity, and the at least one channel 95.

The collection zone 91 can be dimensioned to receive a volume of whole blood sample 5 that can be comprised between 50 and 500 μL. Moreover, the collection zone 91 can be aimed at being punched in order to allow the collection of a component of the whole blood sample 5 (represented on FIGS. 7A-8B). The collection zone 91 of the pattern 9 can have a substantially parallelogram shape and the at least one storage zone 93 can further have a substantially circular shape. Furthermore, the at least one storage zone 93 can be disposed at an angle 97 of the substantially parallelogram shape of the collection zone 91. The pattern 9 may present as many storage zones 93 as the collection zone 91 has angles 97.

According to a particular embodiment, the collection zone 91 can further contain a salt capable of achieving at least partial crenation of red cells 51. The crenation of the red blood cells 51 enables to improve the separation of speed of the components of the whole blood sample 5. This salt can be chosen from the group of alkali metal and alkaline earth metal halogenides and sulfates, and hydrochlorides of organic bases, and more particularly among calcium chloride, potassium sulfate, or guanine hydrochloride. The salt may be present at a concentration in the substrate 3 comprised between 1 and 25% of the total weight of the substrate 3, and more particularly between 10 and 20% of the total weight of the substrate 3.

The storage zone 93 can be aimed at being punched and/or eluted in the case where the component of the whole blood sample 5, such as plasma 55 for example, aimed at being extracted has diffused to the storage zone 93. Furthermore, according to the particular embodiment illustrated by FIG. 2, the at least one storage zone 93 can present pre-perforations 94 facilitating its punching. Such pre-perforations may simplify the automation of a punching process for recovering the plasma that has diffused to the storage zone 93.

According to the specific embodiment illustrated by FIG. 2, the pattern 9 presents a collection zone 91 having a square shape and four storage zones 93 disposed at each angle 97 of the collection zone 91. The collection zone 91 presents a length j of 13 mm and the storage zones 93 present a diameter e of 8 mm, such dimensions for the collection zone 91 and the storage zones 93 being particularly adapted for a whole blood sample 5 of 100 μL. Moreover, each storage zone 93 has a circular shape and is connected to the collection zone 91 by a channel 95 forming a bottleneck between the collection zone 91 and the storage zone 93 associated. The at least one channel 95 has a length 1 that may be comprised between 1 mm and 5 mm and a width w comprised between 1 mm and 3 mm. The width w of the channel 95 of at least 1 mm is imposed due to technological limits. Indeed, it is nowadays not possible to obtain a width w for this channel 95 of less than 1 mm.

Figures 4A, 4B:
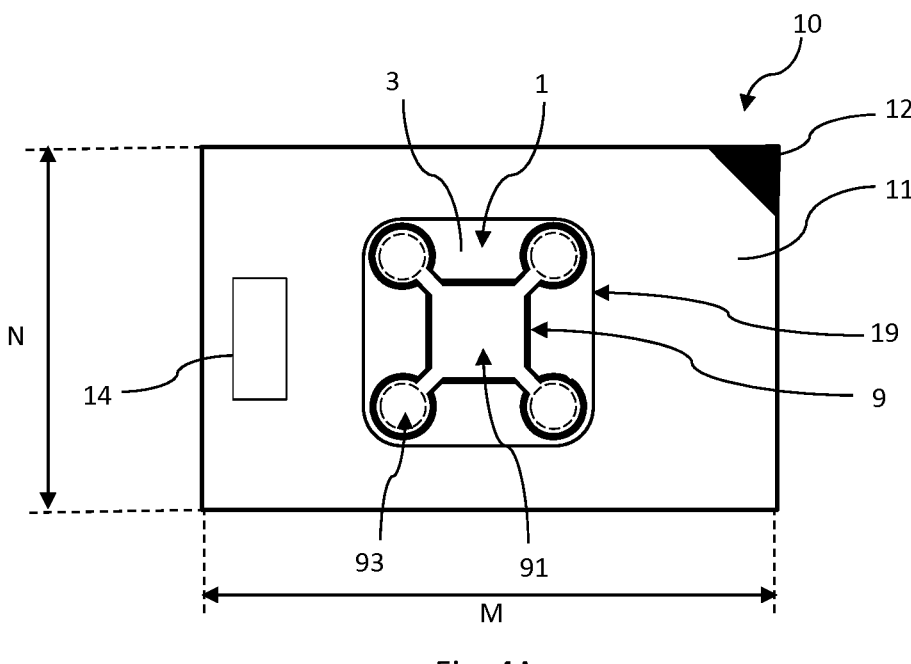
FIG. 4A is a schematic top view of the blood components collection and separation device of FIG. 1 according to a first specific embodiment.
FIG. 4B is a schematic top view of the blood components collection and separation device of FIG. 1 according to a second specific embodiment.

FIGS. 4A and 4B illustrate the blood components collection and separation device 10 according to first and second particular embodiments. According to those particular embodiments, the frame 11 comprises means enabling an automaton (or a human user) to recognize the disposition of this device in a rack for example.

More particularly, according to the first particular embodiment illustrated by FIG. 4A, the frame 11 presents a triangle 12 printed on one corner, said triangle 12 being aimed at enabling an automaton to recognize the direction of the blood components collection and separation device 10. Accordingly, this triangle 12 enables the automation of a blood collection and separation process. Indeed, an automaton can comprise the length M and width N (represented on FIG. 1) of the blood components collection and separation device 10 and the position of the collection zone 91 and the detection of this triangle 12 by vision means (such as a camera for example) may enable the automaton to detect the position of the collection zone 91.

Furthermore, according to the second particular embodiment, illustrated by FIG. 4B, the frame 11 can present a notched angle 13. This notched angle 13 is aimed at enabling an automaton to recognize the direction of the blood components collection and separation device 10. Indeed, as for the first particular embodiment, this notched angle 13 is well known to determine and/or recognize the position of the blood components collection and separation device 10 (or any other flat object) by an automaton.

Still referring to the particular embodiment of FIG. 4B, the blood components collection and separation device 10 further comprises at least two indicators 15 of the collection zone 91. Those indicators 15 are configured for enabling an automaton to detect the collection zone 91 as explained in more details here-after. According to the specific embodiment of FIG. 4B, the indicators 15 are disposed on the blood components collection and separation media 1. In such a case, those indicators 15 can be printed by inkjet or made of the hydrophobic resin forming the pattern 9 during the manufacturing process of the blood components collection and separation media 1. According to a non-represented variant, those indicators 15 can be disposed on the frame 11 of the blood components collection and separation device 10. According to this specific embodiment, the indicators 15 are crosses. However, other designs, not represented here, for those indicators 15 can be easily envisioned.

Figure 5:
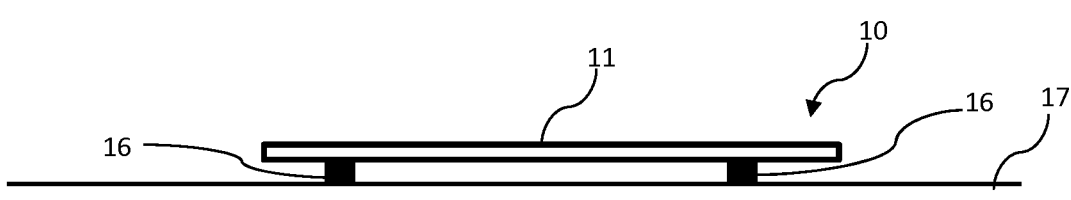
FIG. 5 is a schematic side view of the blood components collection and separation device of FIG. 1 according to a particular embodiment.
Figure 6:
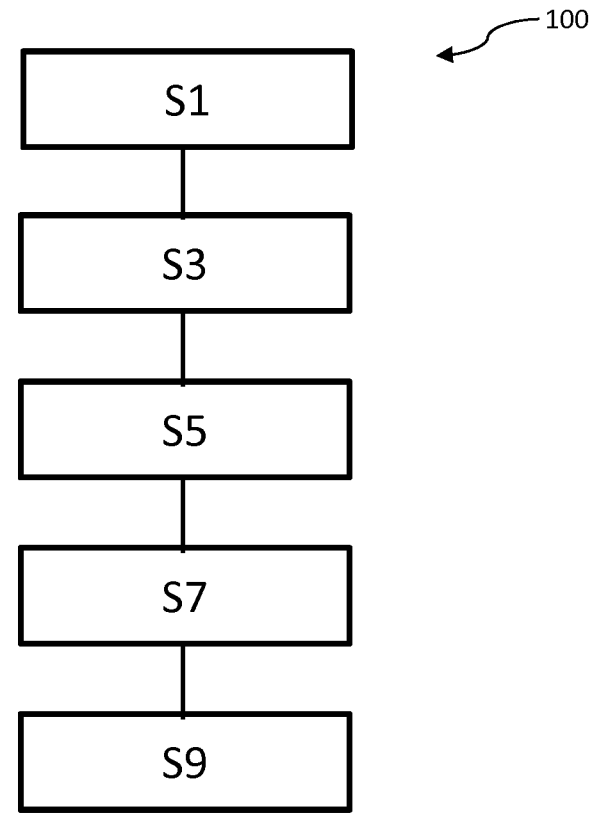
FIG. 6 is a schematic illustration of a blood components separation and extraction process implementing at least the blood collection and separation media of FIG. 2.

FIG. 5 represents the blood components collection and separation device 10 of FIG. 1 according to another particular embodiment in which the frame 11 can further comprise at least two elevating elements 16, and more particularly four elevating elements 16. The elevating elements 16 are configured to be in contact with a support 17, such as a table for example, onto which the blood components collection and separation device 10 is aimed at being disposed to elevate the blood components collection and separation media 1 from said support 17 and prevent any contact between the blood components collection and separation media 1 and the support 17. Thus, those elevating elements

16 enable to prevent any contamination of the blood components collection and separation media 1 by compounds potentially present on the support 17. Such elevating elements 16 can be very useful in the case where the blood components collection and separation device 10 is aimed at receiving a whole blood sample 5 of more than 200 μL for example. Indeed, the blood components collection and separation media 1 (represented on FIG. 2) can curve during the deposition of such a volume of the whole blood sample 5 on same and the contact between the support 17 and the blood components collection and separation media 1 has to be prevented. Those elevating elements 16 can for example be made of the same constituent than the frame 11.

Now referring to FIGS. 6 to 9, there is illustrated a blood components separation and extraction process 100. This process 100 implements a blood components separation and collection media 1 as defined in reference to FIG. 2. According to several embodiments, the target component aimed at being extracted from the whole blood sample can be for example plasma 55, DNA stored in the white cells 53, platelets 52, or lipids stored in the red cells 51.

Figures 7A, 7B, 8A, 8B:
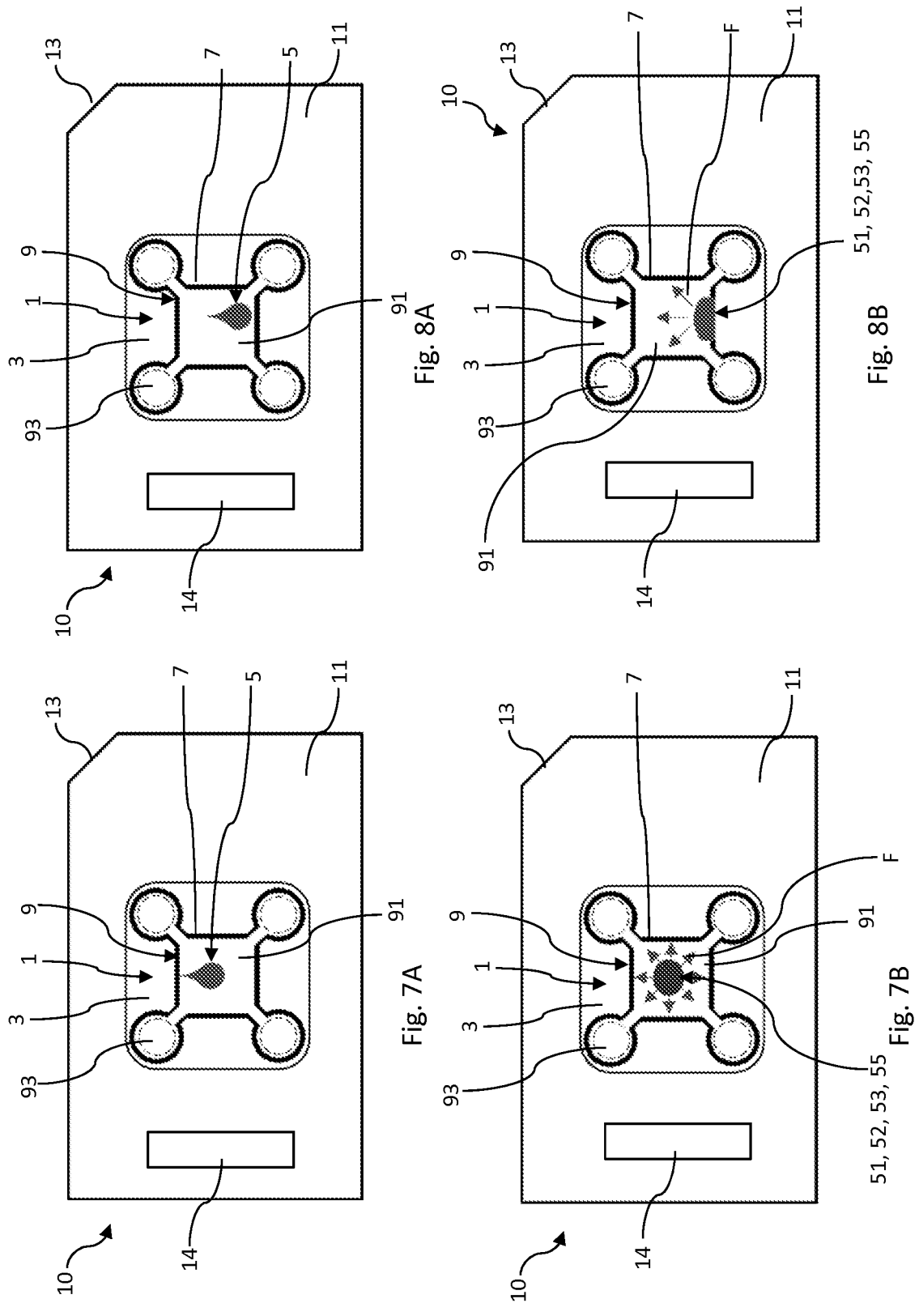
FIGS. 7A and 7B are schematic representations of top views of the blood components collection and separation device during some steps of the blood components separation and extraction process of FIG. 6 according to a first implementation way of said process.
FIGS. 8A and 8B are schematic representations of top views of a blood components collection and separation device during some steps of the blood components separation and extraction process of FIG. 6 according to a second implementation way of said process.

The blood components separation and extraction process 100 implements a deposition step S1 of a whole blood sample 5 in the collection zone 91. This deposition step S1 is better illustrated on FIGS. 7A and 8A. More particularly, this deposition step can be performed at any place in the collection zone 91 without any incidence of the extraction of the blood components of the whole blood sample 5. This deposition can be performed substantially at the center of the collection zone 91 as illustrated by FIG. 7A or at another place as illustrated by FIG. 8A. Such a free place to deposit the whole blood sample 5 enables to simplify this deposition step S1 and also allows a decrease a time necessary to perform such step as well as a potential automation of this deposition step S1. According to the particular embodiments illustrated in FIGS. 7A and 8A, the whole blood sample 5 deposited in the collection zone 91 has a volume comprised between 50 μL and 500 μL, and more preferably of 100 μL.

Then, the blood components separation and extraction process 100 implements an absorption step S3 of the whole blood sample 5 onto the substrate 3. The separation of the blood components of the whole blood sample 5 starts during this absorption step S3. At the same time, the blood components separation and extraction process 100 implements a retention step S5 of the red cells 51, the platelets 52, and the white cells 53 on the substrate 3 in the collection zone 91. Moreover, still in parallel of those absorption S3 and retention S5 steps, the blood components separation and extraction process 100 implements diffusion S7 of at least one component through the substrate 3 to the at least one storage zone 93. Those different steps are illustrated by FIGS. 7B and 8B. More particularly, the arrows F on those figures show the diffusion direction of the whole blood sample 5 in the collection zone 91. As previously disclosed, the several constituents of the whole blood sample 5 will not have the same diffusion speed through the substrate 3 of the blood collection and separation media 1, such difference allowing a separation of the blood constituents of said whole blood sample 5.

Figure 9:
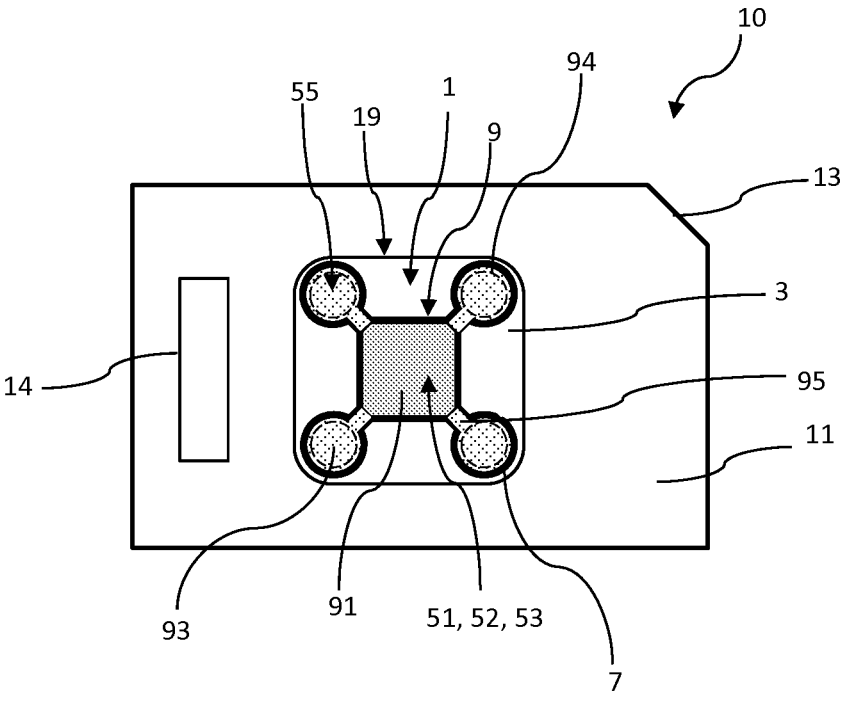
FIG. 9 is a schematic representation of a top view of the blood components collection and separation device of FIGS. 7A-8B after the separation of the blood components on the blood components collection and separation media of FIG. 2.

FIG. 9 illustrates the blood components collection and separation device 10 after those absorption S3, retention S5 and diffusion S7 steps. After those steps, the whole blood sample 5 is separated in its several constituents. More particularly, the red blood cells 51, the platelets 52, and the white blood cells 53 stay in the collection zone 91, and the plasma 55 is in the storage zones 93. Accordingly, it is easy to collect the constituent of the whole blood sample 5 expected. As represented on FIG. 9, all the pattern 9 will contain the several constituents of the whole blood sample 5 whatever where the whole blood sample 5 has been deposited (see FIGS. 7A and 8A). The diffusion of this sample in all the pattern 9 formed by the boundary walls 7 is due to the channels 95 connecting the storage zones 93 to the collection zone 91. Moreover, after those steps, the blood components separation and extraction process 100 implements an extraction step S9 of at least one target component stored in the substrate 3 of the blood components collection and separation media 1. According to a first particular embodiment, the at least one target component can be stored in the at least one storage zone 93 and the extraction step S9 of said at least one target component is performed by punching at least one part of said at least one storage zone 93 or by eluting said at least one target component from the at least one storage zone 93. According to a second particular embodiment, the at least one target component can be stored in the collection zone 91 and the extraction step S9 of said at least one target component is performed by punching at least one part of said collection zone 91 or by eluting said at least one target component from the collection zone 91. According to the particular embodiment of FIG. 9, the target component is plasma 55 and is aimed at being extracted by punching. At this end, the storage zones 93 present preperforations 94 to facilitate the punching of those zones and accordingly improve the efficiency of the extraction step S9.

Furthermore, this blood components separation and extraction process 100 can be aimed at being implemented by an automaton. In such a case, the deposition step S1 is directly implemented by the automaton and the extraction step S9 of performed directly by the automaton after a given time, said given time depending for example on the volume of the whole blood sample 5, or the porosity of the substrate 3 forming the blood components collection and separation media 1. In such a case, the blood components collection and separation device 10 presents the at least two indicators 15 (represented on FIG. 4B) to enable the automaton to detect the collection zone 91. More particularly, the collection zone 91 can be disposed between the indicators 15 when only two are present. The form or the features of those indicators 15 can be imposed by a customer for example in order to be adapted to the automaton he sells.

The several embodiments described here-above are examples given in an illustrative manner and not a limitative one. Indeed, the man skilled in the art can envision other ranges for the length M and the width N of the blood components collection and separation device 10; or adapt the flow pore sizes of the substrate 3, the depth d of the substrate 3 without departing from the teachings of the present specification. Furthermore, the man skilled in the art can adapt the kinds and properties of additives aimed at being added to the fibrous web in order to change the properties of the substrate 3. Then, the dimensions of the collection zone 91, of the storage zone 93 and of the channels 95 can be changed to be adapted to the volume of the whole blood sample 5, and also envision greater volumes of whole blood samples 5 without departing from the teachings of the here-above disclosed embodiments. Moreover, the number of indicators 15 as well as their shape can be changed without departing from the present teachings. Then, other elements than the triangle 12 or the notched angle 13 can be envisioned to determine the position of the blood components collection and separation device 10.

Thus, it is possible to simplify the deposition and the extraction of blood components from a whole blood sample 5 due to the blood components collection and separation media 1 as disclosed here-above. Indeed, the pattern 9, comprising at least one channel 95, formed by the boundary walls 7 enable a direction of the plasma 55 to the at least one storage zone 93. Moreover, this pattern 9 allows a simplification of the deposition of the whole blood sample 5, because it is only necessary to dispose the whole blood sample 5 anywhere in the collection zone 91, the several components being then separated through the substrate 3 and the diffusion of those components in the several zones of the pattern 9 being allowed by the at least one channel 95. Furthermore, such a blood components collection and separation media 1 enables an automation of the blood components separation and extraction process 100.

The invention claimed is:

1. Blood components collection and separation media (1) comprising: a substrate (3) configured to be wetted by a whole blood sample (5), the substrate (3) having a maximal flow pore size comprised between 8 μm and 35 μm, such maximal flow pore size enabling the retention of at least red cells (51) on the surface of the substrate (3), characterized in that the blood components collection and separation media (1) further comprises boundary walls (7) extending at least through a whole depth (d) of the substrate (3) which is a fibrous web and which forms a pattern (9) into said substrate (3), said boundary walls (7) being made of a hydrophobic resin, and in that the pattern (9) within the substrate (3) and formed by the boundary walls (7) comprises:

a collection zone (91) aimed at receiving the whole blood sample (5);

at least one storage zone (93) aimed at collecting at least one component of the whole blood sample (5) after its separation through the substrate (3); and at least one channel (95) connecting the collection zone (91) to the at least one storage zone (93), the at least one channel (95) forming a bottleneck between the collection zone (91) and the at least one storage zone (93).

2. Blood components collection and separation media (1) according to claim 1, wherein the substrate (3) has a mean flow pore size comprised between 2.5 μm and 5 μm.

3. Blood components collection and separation media (1) according to claim 1, wherein the hydrophobic resin forming the boundary walls (7) is chosen among photo-curable resins, UV-curable resins, or thermosetting resins.

4. Blood components collection and separation media (1) according to claim 1, wherein the hydrophobic resin is chosen among fluorinated resins, modified fluorinated resins, latexes, glycol ether acrylates, acrylate esters, or a combination thereof.

5. Blood components collection and separation media (1) according to claim 1, wherein the collection zone (91) of the pattern (9) has a substantially parallelogram shape; and wherein the at least one storage zone (93) is disposed at an angle (97) of the substantially parallelogram shape of the collection zone (91); and wherein the pattern (9) comprises as many storage zones (93) as the collection zone (91) has channels (95).

6. Blood components collection and separation media (1) according to claim 1, wherein the at least one storage zone (93) has a substantially circular shape.

7. Blood components collection and separation media (1) according to claim 1, wherein the at least one channel (95) has a length (1) comprised between 1 mm and 5 mm and a width (w) comprised between 1 mm and 3 mm.

8. Blood components collection and separation media (1) according to claim 1, wherein the fibrous web comprises:

first fibers, said first fibers being chosen among glass micro-fibers or synthetic micro-fibers;

second fibers, said second fibers being chosen among fibrillated fibers; and a hydrophilic binder.

9. Blood components collection and separation media (1) according to claim 8, wherein the hydrophilic binder is at least one of latex binders, polyvinyl alcohol binders, styrene-butadiene binders, vinyl-acetate binders, polysaccharide binders or protein binders.

10. Blood components collection and separation media (1) according to claim 8, wherein the fibrous web comprises between 5 and 7% by weight of the hydrophilic binder.

11. Blood components collection and separation media (1) according to claim 1, wherein the boundary walls (7) forming the pattern (9) exceed one surface of the substrate (3).

12. Blood components collection and separation media (1) according to claim 1, wherein the collection zone (91) further contains a salt capable of achieving at least partial crenation of red cells (51), the salt being chosen from the group of alkali metal and alkaline earth metal halogenides and sulfates, and hydrochlorides of organic bases.

13. Blood components collection and separation device (10), aimed at separating and collecting at least one component of a whole blood sample (5), wherein the blood components collection and separation device (10) comprises at least the blood components collection and separation media (1) according to claim 1 and a frame (11) surrounding the blood components collection and separation media (1).

14. Blood components separation and extraction process (100), wherein the process (100) implements a blood components collection and separation media (1) according to claim 1 and the process (100) comprises the following steps:

depositing (S1) of a whole blood sample (5) in the collection zone (91);

absorbing (S3) of the whole blood sample (5) onto the substrate (3);

retaining (S5) of the red cells (51), the platelets (52) and the white cells (53) on the substrate (3) in the collection zone (91);

diffusing (S7) of at least one component through the substrate (3) to the at least one storage zone (93); and extracting (S9) at least one target component stored in the substrate (3) of the blood components collection and separation media (1).

15. Blood components separation and extraction process (100) according to claim 14, wherein the at least one target component is stored in the at least one storage zone (93) and wherein the extraction step (S9) of said at least one target component is performed by punching at least one part of said at least one storage zone (93) or by eluting said at least one target component from the at least one storage zone (93).

16. Blood components separation and extraction process (100) according to claim 14, wherein the at least one target component is stored in the collection zone (91) and wherein the extraction step (S9) of said at least one target component is performed by punching at least one part of said collection zone (91) or by eluting said at least one target component from the collection zone (91).

17. Blood components separation and extraction process (100) according to claim 14, wherein the whole blood sample (5) deposited in the collection zone (91) has a volume comprised between 50 µL and 500 µL.

18. Blood components separation and extraction process (100) according to claim 14, wherein the target component aimed at being extracted from the whole blood sample (5) is plasma (55).

19. Blood components separation and extraction process (100) according to claim 14, wherein the target component aimed at being extracted from the whole blood sample (5) is DNA, said DNA being stored in the white cells (53).

20. Blood components separation and extraction process (100) according to claim 14, wherein the target component aimed at being extracted from the whole blood sample (5) is lipids, said lipids being stored in the red cells (51).

* * * * *